United States Patent
Avram

(10) Patent No.: US 6,586,608 B1
(45) Date of Patent: Jul. 1, 2003

(54) LIPIDIC CALCIUM COMPOUNDS AND USE FOR TREATMENT OF OSTEOPOROSIS

(76) Inventor: Elena Avram, 545 W. End Ave., Apt 8E, New York, NY (US) 10024

( * ) Notice: Subject to any disclaimer, the term of this patent is extended or adjusted under 35 U.S.C. 154(b) by 0 days.

(21) Appl. No.: 10/261,959

(22) Filed: Oct. 1, 2002

(51) Int. Cl.[7] .................................................. C11C 1/00
(52) U.S. Cl. ...................................... 554/156; 514/425
(58) Field of Search ........................... 554/156; 514/425

(56) References Cited

U.S. PATENT DOCUMENTS

| | | | | |
|---|---|---|---|---|
| 4,649,152 A | * | 3/1987 | Revici | 514/425 |
| 4,772,467 A | | 9/1988 | Pak | 424/127 |
| 5,128,374 A | | 7/1992 | Kochanowski | 514/574 |

OTHER PUBLICATIONS

Donangelo, C.M., "Calcium and Osteoporosis," Arch Latinoam Nutr Jun. 1997;47(2 Suppl 1):13–6.

Dowd, R., "Role of Calcium, Vitamin D, and Other Essential Nutrients in the Prevention and Treatment of Osteoporosis," Nurs Clin North Am Sep. 2001;36(3):417–31, viii.

Heaney, R.P., "Calcium, Dairy Products and Osteoporosis," J Am Coll Nutr Apr. 2000;19(2 Suppl):83S–99S.

Kanis, J.A., "The Use Of Calcium in the Management of Osteoporosis", Bone Apr. 1999;24(4):279–290.

Nordin, B.E., "Calcium and Osteoporosis," Nutrition Jul.–Aug. 1997;13(7–8):664–86.

Revici, Emanuel, Research in Physiopathology as Basis of Guided Chemotherapy *With Special Application to Cancer*, 401–402 (D. Van Nostrand Company, Inc.) (1961).

* cited by examiner

*Primary Examiner*—Deborah D. Carr
(74) *Attorney, Agent, or Firm*—Winston & Strawn

(57) ABSTRACT

A method for making a composition containing calcium incorporated into a fatty acid or fatty ester compound and the compositions produced by this method. These compositions can be administered to a patient to increase the calcium content of cells or tissue having a calcium deficiency or to treat at least some of the symptoms of diseases or adverse effects caused by this calcium deficiency.

21 Claims, No Drawings

LIPIDIC CALCIUM COMPOUNDS AND USE FOR TREATMENT OF OSTEOPOROSIS

FIELD OF THE INVENTION

The present invention relates to a method to treat various conditions resulting from calcium deficiency and preparation of the same. Specifically, the invention relates to the administration of novel calcium-in-oil reaction products for the treatment of osteoporosis.

BACKGROUND OF THE INVENTION

Calcium is an essential nutrient that is involved in many physiological processes, including nerve and muscle functions. The phosphate salts of calcium provide mechanical rigidity to the bones and teeth, where 99% of the body's calcium resides. Calcium in the skeleton has the additional role of acting as a reserve supply of calcium to meet the body's metabolic needs in states of calcium deficiency. Calcium deficiency is easily induced because of the obligatory losses of calcium via bowel, kidneys, and skin. Nutritional and metabolic deficiencies of calcium can have broad-ranging adverse effects. Many of these effects are manifested through deficiencies in the structure, function and integrity of the skeletal system.

The most common metabolic bone disorder is osteoporosis. Osteoporosis is a crippling disease that emerges as an important public health problem in developed as well as developing countries. The clinical condition of osteoporosis is characterized mainly by loss of bone mineral mass, rendering bones more fragile and susceptible to fracture. In humans, osteoporosis is a common feature of aging.

Nutritional therapies for osteoporosis have been proposed. Studies demonstrate that, in general, adequate calcium intake during lifetime contributes to a decreased risk of osteoporosis. Many commercial preparations, typically containing calcium carbonate, are also available. Calcium chloride, calcium gluceptate, calcium gluconate, calcium phosphate, calcium citrate, and other calcium salts have also been described for use in calcium supplement. The use of calcium citrate, for example, is described by Pak in U.S. Pat. No. 4,772,467. Also, U.S. Pat. No. 5,128,374 by Kochanowski teaches the use of calcium citrate malate as a calcium supplement.

Currently, available calcium products have proven of very limited help in treating osteoporosis and other pathological conditions including arthritis, heart disease, Paget's disease, multiple sclerosis, and periodontal conditions. Pathological lesions typically contain free lipids. Currently available non-lipidic calcium formulations have minimal effect on these lesions because the calcium formulations are not taken up effectively by the cells.

The present invention now addresses this problem by providing new formulations and treatment methods for administering calcium to a subject.

SUMMARY OF THE INVENTION

It has now been discovered that calcium can be administered by way of a simple formulation where calcium is incorporated into a lipid by bonding calcium to the non-polar part of the lipid. It has also been found that the lipid-incorporated calcium is much more active biologically then non-lipidic formulations that contain calcium.

The present invention thus relates to novel compositions of lipids which include calcium incorporated therein. There compositions are lipid calcium or calcium-in-oil reaction products that are made by adding a calcium compound to a lipid component and heating the lipid component to a temperature of at least about 230° C. for a sufficient time to incorporate a predetermined amount of calcium into the lipid. At least about 0.1% by weight of calcium should incorporated, but preferably between 1 and 10% by weight are incorporated.

The compositions of the invention may be administered to a patient who has cells or tissues that are deficient in calcium to address the problem. One particular treatment is for subjects experiencing symptoms of osteoporosis to control pain, as well as to treat symptoms of diseases caused by cells and tissue deficient in calcium. The incorporated lipidic calcium is taken up preferentially by free lipids in abnormal cells or tissue, thus providing an increased level of calcium which is useful for effectively treating osteoporosis or other pathological conditions involving calcium deficiency.

DETAILED DESCRIPTION OF THE PREFERRED EMBODIMENTS

In general, abnormal cells and tissues in the body have free lipids. Thus, the invention is based on the recognition that a lipid or compound having a lipidic character introduced into the body can be selectively taken up by these abnormal cells.

Calcium intervenes in the body's action against pathological conditions. In these cases, calcium is mobilized from different parts of the body in the form of lipidic compounds, and these lipidic-calcium compounds are taken up specifically by lesions through abnormal free lipids contained in the lesions. Insufficient intervention of calcium in the body's defense against such lesions is due to the insufficient lipidic action of currently available calcium formulations. Accordingly, calcium compounds having lipidic properties have been found to be useful as a therapeutic agent for patients who have calcium deficient pathological conditions such as osteoporosis.

Calcium can be incorporated in the molecule of a fatty acid by heating together an organic or inorganic salt of calcium with a lipid. Preferably, the lipid is previously oxidized by being heated and mixed with air or oxygen. The mixtures of calcium and lipids are heated at a temperature of at least about 230° C. for a time until an exothermic reaction is observed, which reaction indicates the incorporation is taking place.

Examples of the calcium/lipid compositions that can be used according to the invention include the reaction products of allylic unsaturated lipids and a calcium compound. These reaction products are produced by heating a liquid composition containing a lipid, structurally characterized by allylic unsaturation with a calcium salt. Any calcium salt may be used in the invention, but preferably, the calcium salt is an organic calcium salt such as calcium acetate or calcium carbonate. The liquid is preferably oxidized for example, by bubbling air or oxygen through the reaction mixture.

The allylic unsaturated compound is preferably a naturally occurring oil containing polyunsaturated fatty esters, such as an animal, vegetable, or fish oil, and particularly, polyunsaturated vegetable oils. Sesame oil, a vegetable oil consisting largely of triglycerides, is the most advantageous oil for use in the present compositions.

The composition utilized should contain a significant percentage of molecular species having allylic moieties to render the compositions useful according to the invention. Such moieties are indicated by the following partial structures —CH=CH—CH$_2$—CH=CH— and/or —CH=CH—CH=CH—CH$_2$—. As indicated, the unsaturation can be conjugated or nonconjugated, but the composition must contain allylic methylene hydrogens.

Such compositions may initially be oxidized or heated in the presence of air or oxygen at the temperature range between about 100° C. and about 150° C. The oxygen can be obtained by merely heating the composition in a vessel which is open to the atmosphere, but preferably and advantageously, the source of oxygen is a gas such as air which is introduced into the oil with agitation during the heating step. Oxygen or air can be injected into the heated oil wherein the introduction of air provides a source of agitation.

The heating step is conducted for a period of from about 15 minutes to about two hours. The temperature should be maintained at an upper limit within the range of about 230° C. to 250° C., and preferably about 235° C. to 240° C. These temperature limitations are based on a heating time of about one-half hour. The temperatures can be altered within limits depending on the time of heating. For example, when the temperature is about 235° C., the time is about one-half hour, while temperatures as high as 250° C. require a shorter period of time for heating. Higher temperatures for a prolonged period of time tend to degrade the composition and should thus be avoided.

Agitation, by stirring for example, aids in the reaction, and experiments to date indicate that a fairly violent stirring is advantageous. The introduction of air into the mixture during the heating is also very advantageous, particularly when the mixture is not subject to prolonged heating and thus, is the preferred method. Preferably, the mixing or stirring can be accomplished with the introduction of the air.

After the reaction has taken place, the mixture is cooled. The remaining fluid is ready for use after appropriate sterilization for injection or incorporated into capsules, such as gelatin, for oral administration.

The precise nature of the compositions which result from the above-described treatment or the identity of the effective component or components is not presently known. It is known, however, that these compositions do include calcium. Although any amount above 0.1% of calcium incorporated into the composition is useful, a proportion of calcium in the range of about 1 to 10% by weight has been found to be preferred. As mentioned above, any calcium salt may be used, but an organic salt of calcium, such as calcium carbonate or calcium acetate, is preferred, with the calcium bonding the eleostearic acid present in the oil.

The products obtained have the calcium incorporated in general at the level of the double bonds of the different unsaturated fatty acids, this causes their toxicity to be exceptionally low. The injection of 1 ml of a production having 5% calcium to a mouse does not kill it.

The incorporated calcium composition may be administered orally, by injection, sublingually or rectally in the appropriate formulation.

The incorporated calcium is believed to be absorbed by the abnormal cells, thus compensating for their low calcium content. This treatment produces objective and subjective improvement in the conditions, of patients having a variety of disease based upon such abnormal cells. Osteoporosis is an example of diseases in which low cellular calcium abnormal cells are found. By increasing cellular calcium, the progression of osteoporosis is slowed.

Such low cellular calcium abnormal cells are believed to cause a catabolic imbalance in the body. This catabolic imbalance can be analyzed and diagnosed by blood and urine analyses. A low eosinophilia (below 100/cmm), a high red cell sedimentation rate (above 15 ml/1 hour), a high serum (above 4.5 mEq), a urine acid pH (below 7), high specific gravity (above 1.016), low surface tension (below 89 dynes/cm), and low calcium or chloride excretion are indications of a catabolic imbalance. (The opposite analyses would indicate a anabolic imbalance.)

These analyses and clinical manifestations have to be changed by the administration of the incorporated calcium compound. In a 5% calcium incorporated preparation, amounts from about ⅒to 2 ml daily are predilectly used for the treatment of this catabolic imbalance. For other conditions with anabolic imbalances, doses from about 2 to 10 ml daily are preferably used. In general the higher the dose used, the better are the clinical results.

The fundamental difference in action in the body between non-lipidic calcium and lipid-incorporated calcium manifests itself in their effects on certain painful lesions which have a lack of calcium involved in their pathogenesis. The lipid-incorporated calcium in the present invention brings calcium directly to pathological lesions to be taken up by the free lipids of the lesions. Thus, the lipid-incorporated calcium is much more active biologically than this element when it is not incorporated in a lipid. Non-lipidic calcium compounds administered over a long period of time had little or no effect on the pain. Administration of our lipid-incorporated calcium, however, controlled this same pain in a few days.

In addition to successful treatment of osteoporosis, good results were also obtained in the use of the incorporated calcium compounds to treat other pathological conditions where all available calcium products have proven of very limited help. These conditions include: arthritis, heart diseases, Paget's disease, multiple sclerosis, and periodontal conditions.

The incorporated calcium composition may be administered together with different additional agents, including analgesics, vitamins, minerals, antioxidants and the like, depending upon the route of administration.

Specific preferred additional agents include epichlorohydrin (i.e., 1-chloro 2,3-epoxy propane), magnesium thiosulfate, or n-butanol. It is preferable that hydrolyzed epichlorohydrin is incorporated in the calcium compositions and that at least about 0.05% by weight of hydrolyzed epichlorohydrin, and more preferably that between about 0.1 and 1.5% by weight is incorporated in the calcium compositions. These amounts have been found to be advantageous, but can be higher or lower if desired.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

What is claimed is:

1. A method of making a composition which comprises:
    selecting at least one fatty acid or fatty ester compound having an allylic unsaturation of the type —CH=CH—CH$_2$—CH=CH— and/or —CH=CH—CH=CH—CH$_2$—;
    adding to said compound a calcium salt to form a mixture;
    heating said mixture to at least about 230° C. for a sufficient period of time to incorporate at least about 0.1 by weight calcium into the compound;

cooling the mixture; and recovering the calcium-incorporated compound as the remaining fluid of the mixture.

2. The method of claim 1 wherein the calcium salt is an organic salt and the fatty acid or fatty ester compound is oxidized by mixing the compound with air and heating the mixture.

3. The method of claim 1 wherein the fatty acid or fatty ester compound is heated at a temperature range of about 230° C. to 250° C. for a time of at least about fifteen minutes to two hours so as to incorporate at least 1% by weight calcium into the composition.

4. The method of claim 1 wherein the fatty acid or ester compound is a vegetable oil and the heating step is conducted to incorporate at least 1% by weight of calcium into the oil.

5. The method of claim 1 wherein the calcium salt is calcium carbonate or calcium acetate.

6. The method of claim 1 further comprising the step of adding epichlorohydrin to the mixture.

7. The method of claim 6 wherein at least about 0.05% by weight of epichlorohydrin is incorporated into the mixture.

8. The method of claim 1 wherein air or oxygen is added during the heating step.

9. The method of claim 8 which further comprises agitating the mixture during the heating step.

10. A lipidic calcium composition comprising at least one fatty acid or fatty ester compound having the composition produced by the method of claim 1 and which includes calcium incorporated therein in an amount of at least 0.1% by weight.

11. The composition produced by the method of claim 1.

12. The lipidic calcium composition of claim 10 further comprising epichlorohydrin.

13. The composition of claim 12, wherein at least about 0.05% by weight is epichlorohydrin.

14. The lipidic calcium composition of claim 11 further comprising epichlorohydrin.

15. The composition of claim 14, wherein at least about 0.05% by weight is epichlorohydrin.

16. A method for increasing calcium content of cells or tissue that have free lipids and a calcium deficiency which comprises administering to a subject in need of such treatment the composition of claim 10 in an amount to sufficient to increase calcium content of such cells or tissues.

17. A method for increasing calcium content of cells or tissue having a calcium deficiency which comprises administering to a patient having said calcium deficient cells or tissue a sufficient amount of the composition of claim 11.

18. The method of claim 16 wherein the composition is administered to a patient exhibiting symptoms of osteoporosis.

19. The method of claim 17 wherein the composition is administered to a patient exhibiting symptoms of osteoporosis.

20. The method of claim 16 wherein about 1/10 to 10 ml of the composition is daily administered to the patient.

21. The method of claim 17 wherein about 1/10 to 10 ml of the composition is daily administered to the patient.

* * * * *